(12) United States Patent
Zechlin et al.

(10) Patent No.: US 7,517,829 B2
(45) Date of Patent: Apr. 14, 2009

(54) PROCESS FOR THE PRODUCTION OF RANEY NICKEL CATALYSTS AND THEIR USE IN THE HYDROGENATION OF ORGANIC COMPOUNDS

(75) Inventors: Joachim Zechlin, Neuss (DE); Gerhard Wegener, Mettmann (DE); Hans Warlimont, Dresden (DE)

(73) Assignee: Bayer MaterialScience AG, Leverkusen (DE)

( * ) Notice: Subject to any disclaimer, the term of this patent is extended or adjusted under 35 U.S.C. 154(b) by 852 days.

(21) Appl. No.: 10/932,627

(22) Filed: Sep. 2, 2004

(65) Prior Publication Data

US 2005/0107251 A1     May 19, 2005

(30) Foreign Application Priority Data

Sep. 8, 2003    (DE) ................ 103 41 269

(51) Int. Cl.
*B01J 25/02* (2006.01)
*B22D 11/06* (2006.01)
*C07C 209/36* (2006.01)

(52) U.S. Cl. ............... 502/301; 164/480; 564/422

(58) Field of Classification Search ............ 564/422, 564/423; 502/301; 164/428, 480
See application file for complete search history.

(56) References Cited

U.S. PATENT DOCUMENTS

| | | | | |
|---|---|---|---|---|
| 4,287,365 A | 9/1981 | Becker et al. | ........ | 564/422 |
| 4,792,626 A | 12/1988 | Becher et al. | ........ | 564/422 |
| 4,907,641 A | 3/1990 | Gaspar | ........ | 164/423 |
| 5,090,997 A | 2/1992 | Birkenstock et al. | ........ | 75/338 |
| 5,170,837 A | 12/1992 | Gaspar | ........ | 164/429 |
| 6,395,934 B1 | 5/2002 | Wegener et al. | ........ | 564/422 |
| 6,474,402 B1 * | 11/2002 | Sauer et al. | ........ | 164/428 |

FOREIGN PATENT DOCUMENTS

GB      2 070 479      9/1981

OTHER PUBLICATIONS

Andersen O et al: "Melt extracted fibres boost porous parts" Metal Powder Report, MPR Publishing Services, Shrewsbury, GB, Bd. 54, Nr. 7-8, Jul. 1999, Seiten 30-34, XP004289572.
Maringer et al.: J. Vac. Sci, Technol., Bd. 11, Nr. 6, 1974, Seiten 1067-1071, XP009037689.
Lotze G. et al.: "Fundamentals of fibre formation during melt extraction" Materials Science and Engineering, 1991, Seiten 680-683, XP002300390.

* cited by examiner

*Primary Examiner*—Wayne Langel
*Assistant Examiner*—James Fiorito
(74) *Attorney, Agent, or Firm*—Noland J. Cheung; N. Denise Brown (57) ABSTRACT

The invention relates to a process for the production of Raney nickel catalysts. In this process, the melt of an alloy comprising from 40 to 95 wt. % aluminum, from 5 to 50 wt. % nickel, 0 to 20 wt. % iron, from 0 to 15 wt. % of one or more transition metals selected from the group consisting of cerium, cerium mixed metal, vanadium, niobium, tantalum, chromium, molybdenum and manganese, and, optionally, additional glass-forming elements, is brought into contact with one or more rotating cooling rollers or cooling plates and is allowed to cool and solidify thereon. The cooling rollers have a surface structured by means of transverse grooves, and the cooling plates have a surface structured by means of grooves extending outwards from the axis of rotation. The rapidly solidified alloy on the cooling rollers or the cooling plates is then subjected to treatment with one or more organic or inorganic bases.

5 Claims, 3 Drawing Sheets

PROCESS FOR THE PRODUCTION OF RANEY NICKEL CATALYSTS AND THEIR USE IN THE HYDROGENATION OF ORGANIC COMPOUNDS

BACKGROUND OF THE INVENTION

The present invention relates to a process for the production of Raney nickel catalysts having a long useful life and high product selectivity. This invention also relates to the hydrogenation of organic compounds, particularly the hydrogenation of aromatic nitro compounds prepared in the presence of these Raney nickel catalysts.

The production and use of Raney nickel as a hydrogenation catalyst for aromatic nitro compounds, such as, for example, nitrobenzene, nitrotoluenes, dinitrotoluenes, chlorinated nitro aromatic compounds and the like, is known and has been described. See e.g. R. Schröter, Angew. Chem. 1941, 54, 229 or EP-A-0 223 035. The production of Raney nickel catalysts is usually carried out starting from a pre-alloy comprising aluminium and nickel and optionally one or more further sub-group metals as catalyst precursor. The alloy is obtained, for example, by melting or reactively grinding the starting metals. Raney nickel catalysts can be modified by alloying the starting alloy with other metals in order to improve their activity, selectivity and stability, especially at elevated temperatures. This doping of the catalyst by addition of a very wide variety of metals to the Al—Ni melt of the catalyst precursors is known and described in, for example, DE-A 40 01 484 and DE-A 35 37 247. The catalyst precursors are produced by atomisation of the Al—Ni metal melt, or are cast and then comminuted mechanically. The catalyst is then freed by extracting some or all of the aluminium from the alloy using a base as described in, for example, DE-A 27 13 374. The catalytic activity of the catalysts obtained from the alloys is dependent inter alia on the qualitative and quantitative composition of the alloy, the structure and constitution of the alloy, and accordingly, on the resulting structure and constitution of the catalyst.

The hydrogenation of aromatic nitro compounds is a reaction that is frequently carried out on a large scale. Raney nickel catalysts are often used for this purpose. The catalyst lifetime, product selectivity, structures and constitution of the starting alloys and the solidification rate are scarcely correlated. In the ternary systems of Al—Ni-additional metal in particular, the starting alloy may contain a large number of phases which exhibit no or only poor activities, high catalyst consumption and low product selectivity in the resulting catalyst. DE-A 19 753 501 describes the use of amorphous, partially amorphous or microcrystalline alloys which are produced by rapid solidification, for the production of RaNi catalysts, to increase the catalyst lifetime, and accordingly, to reduce the catalyst consumption. The production processes described therein for the pre-alloy include the pouring out of a metal melt onto a rotating cooling roller or into the gap between two rotating cooling rollers, as well as melt extraction.

According to A. Molnar, G. V. Smith, M. Bartok, Advances in Catalysis, 36, 329-383 (1989), high cooling rates or solidification rates of from $10^4$ to $10^7$ K/s can be achieved by melt spinning or by the production of metal strips. This can be effected, for example, by pressing an alloy melt onto or into the gap between two rotating cooling rollers or by pouring out onto a cooled rotating plate, as well as by processes known to the person skilled in the art as the melt extraction process (i.e. melt extraction rapid solidification technology, MERST), or as the melt overflow process (i.e. melt overflow rapid solidification technology, MORST).

In melt overflow technology, a metal melt flows in a thin layer generally over a horizontal overflow edge onto a rotating cooling roller, with rapidly solidified metal fibers or metal flakes being formed. The overflowing of the melt onto the roller is made possible, for example, by tipping the melting crucible, but can also be carried out by displacing the melt by means of, for example, a plunger that dips into the melting crucible. By shrinkage of the alloy as it cools on the cold metal surface, and as a result of the centrifugal force of the rotating roller, the flakes or fibers are thrown from the surface thereof. The melt overflow process can be carried out in air, under an inert gas, or alternatively, in a vacuum chamber.

The technology for the production of the pre-alloy by means of the melt overflow process is described inter alia in U.S. Pat. No. 5,170,837 and also in U.S. Pat. No. 4,907,641.

In melt extraction, a rotating cooling roller provided above the melting crucible comes into contact with the surface of the metal melt and, as a result of the rotation, draws rapidly solidified metal fibers from the melt. By shrinkage of the alloy as it cools on the cold metal surface, and as a result of the centrifugal force of the rotating roller, the flakes or fibers are thrown from the surface thereof.

Melt extraction can be also be carried out in air, under an inert gas, or alternatively, in a vacuum chamber.

The technology for the production of the pre-alloy by means of the melt extraction process is described inter alia in O. Andersen, G. Stephani, Metal Powder Report, 54, 30-34 (1999).

A further method of rapid solidification comprises pouring a metal melt onto a rotating cooling plate, and allowing the rapidly solidified alloy to be thrown tangentially from the plate.

Pouring onto the cooling plate can be carried out in air, under an inert gas, or alternatively, in a vacuum chamber.

In melt overflow technology, melt extraction technology and in the case of pouring out onto rotating rollers or a rotating plate, it is possible, according to A. Molnar, G. V. Smith, M. Bartok, Advances in Catalysis, 36, 329-383 (1989), to achieve cooling rates which are very much greater than $10^4$ K/s. In contrast to conventional rapid solidification processes, such as the atomisation of a metal melt in water, as described, for example, in EP-A-0 437 788, the formation of an undesirable oxide content is largely suppressed in such processes.

In the case of the pouring of a metal melt onto or into the gap between two rotating cooling rollers, in the melt overflow process, in the melt extraction process or in the pouring of a metal melt onto a rotating cooling plate, endless fibres or endless strips are usually produced in the production of ductile metal alloys. The cooling rollers or cooling plates used in the production of such endless fibers or endless strips have surfaces that exhibit no structuring transversely to the direction of rotation. The entire surface of the cooling roller or cooling plate is used for cooling and solidifying the melt, and the cooling capacity is accordingly fully utilised. As a result, it is possible to achieve a very uniform, high solidification speed and the formation of a very homogeneous microcrystallinity. The use of cooling rollers and cooling plates without structuring transversely to the direction of rotation is also advantageous especially because such structures on the surface of the cooling rollers or cooling plates can have an adverse effect on the microstructure of the alloys produced, because the cooling speed at the beginning and at the end of such surface structures on the cooling roller or cooling plate is lower than in the middle. Furthermore, ductile metal alloys are advantageously produced in the form of endless fibers or strips because the formation of agglomerates which have not been rapidly solidified can be suppressed to the greatest possible extent owing to the uniform solidification rate of the alloy on the cooling roller or cooling plate.

However, Raney nickel pre-alloys having a high aluminium content are not ductile, but brittle materials. Therefore, the rapid solidification of RaNi pre-alloys using rotating cooling rollers or cooling plates by, for example, the melt overflow process or the melt extraction process, in accordance with the prior art yields long fragments of fibers or strips of irregular length. These fibers and strips of undefined length tend to interlock and mat in the product container, during conveying and during transportation, are not pourable and have a decidedly low bulk density during filling and transportation.

It is therefore necessary to bring the fibers or strips of the pre-alloy to a processable and transportable size suitable for conveying, transportation and further processing, by means of a grinding process provided downstream. This additional process step requires an additional outlay in terms of apparatus and energy in the production of the pre-alloy. Moreover, the additional energy supplied during grinding alters the metal structure of the pre-alloy and its microstructure. This mechanically induced recrystallisation is described, for example, in *J. Friedrich, U. Herr, K. Samwer, Journal of Applied Physics*, 87, 2464 (2000). If grinding of the pre-alloy is omitted, however, a considerably greater transport volume is required, and conveying of the interlocked and matted alloy, for example, by means of a conveyor belt, a conveyor screw or an air stream, is made considerably more difficult or impossible.

There is therefore a need for a simple and economic process for the production of rapidly solidified RaNi catalysts which are suitable particularly as catalysts for the hydrogenation of nitro aromatic compounds to the corresponding amines wherein the catalysts having long useful lives and high selectivity.

Accordingly, the object of the present invention was to provide Raney nickel catalysts, and a simple and economic process for their production, in which the Raney nickel pre-alloys produced by rapid solidification do not interlock or mat and can be transported and treated further, without additional outlay.

It has now been found that the particle size or fiber size of Raney nickel pre-alloys can be markedly reduced compared with the alloys conventionally obtained by rapid solidification, if cooling rollers structured by means of transverse grooves are used for the pouring out onto or into the gap between two cooling rollers, for the melt extraction or for the melt overflow process, or if cooling plates structured by means of grooves extending outwards from the axis of rotation are used for the pouring out onto a rotating cooling plate. The short fibers or short strips produced according to the invention have a markedly higher bulk density, are pourable, do not tend to mat, and can be transported without difficulty by means of conventional conveyor devices such as, for example, conveyor belts, conveyor screws. Surprisingly, the catalytic properties of the Raney nickel catalysts produced in accordance with the present invention even exceed the catalytic properties of the Raney nickel catalysts produced in accordance with the prior art by rapid solidification on cooling rollers or cooling plates without surface structuring transversely to the direction of rotation. This is seen, for example, in the hydrogenation of dinitrotoluene, in an increased yield of toluylenediamine from dinitrotoluene, and an increased lifetime of the catalyst.

SUMMARY OF THE INVENTION

The present invention relates to a process for the production of Raney nickel catalysts. This process comprises (1) contacting (a) the melt of an alloy which comprises (i) from 40 to 95 wt. % aluminium, (ii) from 5 to 50 wt. % nickel, (iii) from 0 to 20 wt. % iron, (iv) from 0 to 15 wt. % of one or more transition metals selected from the group consisting of cerium, cerium mixed metal, vanadium, niobium, tantalum, chromium, molybdenum and manganese, and, (v) optionally, additional glass-forming elements, with (b) one or more rotating cooling rollers or cooling plates; (2) allowing the melt to cool and solidify on the cooling rollers or cooling plates, and (3) treating the rapidly solidified alloy with one or more organic bases and/or inorganic bases. The suitable cooling rollers have a surface structured by means of transverse grooves, and the suitable cooling plates have a surface structured by means of grooves extending outwardly from the axis of rotation.

BRIEF DESCRIPTION OF THE DRAWINGS

FIG. 1 illustrates cooling rollers of the present invention.

FIG. 3 illustrates a top view of a cooling plate of the invention.

DETAILED DESCRIPTION OF THE INVENTION

The transverse grooves on the surface of the suitable cooling rollers are distinguished by the fact that they extend substantially transversely. That is to say that these transverse grooves extend in a manner such that their principal direction of extension is substantially parallel to the axis of rotation of the cooling roller, and enclose an angle of up to 45° with the axis of rotation.

The transverse grooves of the cooling rollers are preferably straight, but they may also be slightly curved or bent, for example. The transverse grooves preferably extend in the direction of the axis of rotation of the cooling roller over the entire length of the cooling roller. However, constructions in which the transverse grooves extend only over a portion of the length of the roller are also conceivable and suitable for the present invention.

The grooves on the surface of the cooling plates which extend outwardly from the axis of rotation may be straight, for example radial, or be curved, for example arc-shaped. These grooves preferably extend from the axis of rotation to the edge of the cooling plate. However, constructions in which the radial or arc-shaped grooves extend only over a portion of the radius of the plate are also conceivable and suitable for the present invention. Geometries for the grooves on the surface of cooling plates and for the grooves on the surface of cooling rollers which are particularly suitable for specific alloy compositions can readily be determined by means of experiments.

In accordance with the present invention, grooves are understood to be any form of channels, elongated slots or other elongated indentations in the surface. The grooves may have any desired shape. For example, grooves may be triangular, square, semi-circular or semi-oval. The grooves preferably have a maximum depth of from 0.5 to 20 mm and a maximum width of from 0.5 to 20 mm. Particular preference is given to the embodiment wherein the grooves have a depth of from 1 to 5 mm and a width of from 1 to 10 mm.

Cooling rates of greater than $10^4$ K/s are achieved in the process according to the invention.

This invention relates particularly to a process for the production of Raney nickel catalysts. In one embodiment of this process, the alloy melt is allowed to flow in accordance with the melt overflow process from a melting crucible onto a rotating cooling roller, and is allowed to cool and solidify thereon, wherein the surface of the cooling roller is structured by means of transverse grooves.

The invention also relates particularly to an embodiment of the process for the production of Raney nickel catalysts in which, in accordance with the melt extraction process, portions of the melt are removed from the alloy melt by means of a rotating cooling roller that dips into the alloy melt, and are allowed to cool and solidify thereon, with the surface of the cooling roller being structured by means of transverse grooves.

In another embodiment of the present invention which relates especially to a process for the production of Raney nickel catalysts, the alloy melt is poured onto a rotating cooling roller or into the gap between two cooling rollers rotating in opposite directions. The melt is allowed to cool and solidify on the rotating cooling roller or rollers, wherein the surface of the cooling rollers is structured by means of transverse grooves.

Another alternate embodiment of the invention relates especially to a process for the production of Raney nickel catalysts in which the melt is poured onto a rotating cooling plate, and is allowed to cool and solidify thereon. The surface of the cooling plate in this embodiment is structured by means of grooves which extend outwardly from the axis of rotation of the cooling plate.

By chilling a metal (alloy) melt at high cooling rates which are much greater than $10^4$ K/s, it is possible for metastable phases and structures outside the state of equilibrium to be obtained and frozen in the solidified structure. A refinement of the structure, i.e. smaller crystallite sizes, in the range from 1 to 10 μm and below, preferably <2 μm, is thus established in the catalysts according to the invention. If the rapid solidification of the alloy melt is carried out at cooling rates much greater than $10^4$ K/s, then amorphous alloys or alloys having crystalline and amorphous regions, which are referred to as partially amorphous hereinbelow, or completely microcrystalline states are obtained. The term amorphous in connection with metal phases, also classified as metal glasses or supercooled, solid melts, describes the absence of crystallinity.

The formation of amorphous or partially amorphous structures can additionally be positively influenced by the addition of further alloying metals. In the catalyst according to the invention, alloying metals such as the transition metals are used. In particular, transition metals include preferably metals such as, for example, cerium or cerium mixed metal, as well as from 0.5 to 1% yttrium and/or selected sub-group elements, including preferably vanadium, niobium, tantalum, chromium, molybdenum or manganese. Alternatively, further glass-forming main-group elements, such as, preferably boron, silicon, carbon and/or phosphorus, may additionally be present.

The catalysts according to the invention are based on amorphous/partially amorphous or microcrystalline alloys which are produced by rapid solidification of the alloy melt in accordance with the melt overflow technology and also in accordance with the melt extraction technology. These catalysts are produced with the use of structured cooling rollers according to the invention, or by pouring out the alloy onto a rotating plate or cooling roller structured according to the invention, or by pouring out the alloy into the gap between two such cooling rollers. The catalysts of the invention are distinguished from conventional Raney nickel catalysts whose pre-alloys have not been solidified at such a high solidification rate, by a markedly increased product selectivity and catalyst lifetime, particularly at high reaction temperatures, i.e. >120° C. The final product resulting when the catalysts according to the invention are used in the large-scale hydrogenation of organic compounds is increased and the amounts of waste produced are markedly reduced. This effect is advantageous, for example, in the commercial production of 2,4-toluene diamine and/or 2,6-toluene diamine by hydrogenation of dinitrotoluenes or other aromatic nitro compounds, and particularly in those cases of hydrogenation without added solvent.

However, the catalysts produced by the process of the present invention are also distinguished, in comparison with the previously known Raney nickel catalysts produced in the prior art, by an increased yield in the hydrogenation of nitro compounds to the corresponding amines and by an increased lifetime of the catalysts. As previously described, the Raney nickel catalysts of the prior art are produced by rapid solidification of the pre-alloy on cooling rollers or cooling plates wherein the cooling rollers or cooling plates which are free of surface structuring transversely to the direction of rotation.

In accordance with the process of the invention for the production of Raney nickel catalysts from rapidly solidified alloys, or for the production of amorphous, partially amorphous or microcrystalline alloys as catalyst precursors, the alloys used comprise (i) from 40 to 95 wt. % aluminium, (ii) from 5 to 50 wt. % nickel, (iii) from 0 to 20 wt. % iron, and (iv) from 0 to 15 wt. % of one or more transition metals which is selected from the group consisting of cerium, cerium mixed metal, vanadium, niobium, tantalum, chromium, molybdenum and manganese. It is preferred that the alloys comprise (i) from 50 to 90 wt. % aluminium, (ii) from 15 to 50 wt. % nickel, (iii) from 0 to 10 wt. % iron, and (iv) from 0 to 10 wt. % of one or more transition metals selected from the group consisting of cerium, cerium mixed metal, vanadium, niobium, tantalum, chromium, molybdenum and manganese. Particularly preferred are alloys comprising (i) from 60 to 85 wt. % aluminium, (ii) from 15 to 40 wt. % nickel, (iii) from 0 to 6 wt. % iron, and (iv) from 0 to 10 wt. % of one or more transition metals selected from the group consisting of cerium, cerium mixed metal, vanadium, niobium, tantalum, chromium, molybdenum and manganese. The relative %'s by weight of (i), (ii), (iii) and (iv), and optionally, (v) totals 100% by weight of the melt of the alloy.

These alloy melts suitable for the present invention can be produced, for example, by inductive melting of the metals in appropriate weight ratios.

The thickness of the flakes or fibers obtained on the cooling rollers or cooling plates is generally from about 10 to about 150 μm, preferably from about 20 to about 120 μm, and more preferably from about 30 to about 100 μm. The cooling wheel (e.g. the roller or the plate) preferably consists of a base alloy of copper (i.e. Cu), silver (i.e. Ag), an alloy based on copper (Cu) and silver (Ag), or stainless steel. It may also be produced from any other metal materials. The cooling roller can be cooled by means of ambient air, cooled gases, by means of water, or, by any other gaseous or liquid cooling medium.

The freeing of the Raney nickel catalysts is carried out by alkali treatment of the rapidly solidified alloy which is optionally comminuted, using aqueous solutions of one or more organic bases and/or inorganic bases. Suitable bases include, for example, sodium hydroxide, potassium hydroxide, sodium carbonate, potassium carbonate, etc. It is preferred to use sodium hydroxide or potassium hydroxide. It is also preferred that the alkali treatment of the alloy occurs at temperatures of from about 50 to about 150° C. The amount of base used is dependent on the amount of aluminium present in the alloy. The base can be used in a stoichiometric amount, in excess or in a smaller amount, relative to the amount of aluminium. Preference is given to a weight ratio of aluminium to base ranging from about 1:1 to about 1:10, and more preferably to a ratio of from about 1:1.1 to about 1:5. The catalyst can be isolated by, for example, decanting or filtering off some or all of the aqueous solution, and washing repeatedly, followed by decanting or filtering off additional washing solution. Water (e.g. deionised, distilled, drinking water or water for industrial use) or a solution of sodium hydroxide and/or potassium hydroxide in water is used as the washing solution.

The catalysts which can be produced by extraction from the described rapidly solidified amorphous, partially amorphous or microcrystalline alloys comprise residual amounts of (i) from 0 to 15 wt. % aluminium, (ii) from 50 to 100 wt. % nickel, (iii) from 0 to 50 wt. % iron, and (iv) from 0 to 30 wt. % of one or more transition metals selected from the group consisting of cerium, cerium mixed metal, vanadium, niobium, tantalum, chromium, molybdenum and manganese. Catalysts comprising (i) from 0 to 10 wt. % aluminium, (ii) from 60 to 100 wt. % nickel, (iii) from 0 to 30 wt. % iron, and (iv) from 0 to 30 wt. % of one or more transition metals selected from the group consisting of cerium, cerium mixed metal, vanadium, niobium, tantalum, chromium, molybdenum and manganese are preferred. Particularly preferred alloys comprise (i) from 0 to 10 wt. % aluminium, (ii) from 70 to 100 wt. % nickel, (iii) from 0 to 20 wt. % iron metals, and (iv) from 0 to 25 wt. % of one or more transition metals selected from the group consisting of cerium, cerium mixed metal, vanadium, niobium, tantalum, chromium, molybdenum and manganese. The relative %'s by weight of (i), (ii), (iii) and (iv), totals 100% by weight of the catalyst of the present invention.

The invention relates also to a process for the hydrogenation of organic compounds in the presence of the described catalysts. More specifically, this process is for the hydrogenation of aromatic nitro compounds.

Suitable starting materials to be used as organic compounds in the hydrogenation process include particularly aromatic nitro compounds, such as, for example, nitrobenzene, the isomers and mixtures of isomers of nitrotoluene, chlorinated nitro aromatic compounds, dinitronaphthalene and, preferably, the isomers and isomeric mixtures of dinitrotoluene. The nitro compounds are preferably hydrogenated in a solventless manner, i.e. without the use of added solvent, at temperatures of from about 100 to about 250° C., preferably from about 120° C. to about 200° C., and at a pressure of from about 5 to about 100 bar, preferably at from about 10 to about 50 bar, in the presence of the catalyst suspended in the reaction medium. The reaction medium is composed substantially of product, correspondingly formed water and the gas phase.

It is also possible for a solvent, such as, for example, an alcohol, preferably methanol or 2-propanol, to be added to the reaction medium. The hydrogenation of other nitro compounds is often carried out in a solvent, such as, for example, in an alcohol, preferably in methanol or 2-propanol, at a pressure of from about 5 to about 200 bar.

The hydrogenation can be carried out either continuously or discontinuously in the conventional reactors. In the case of a continuous procedure or process, the amount of nitro compound fed into the reactor corresponds to the amount of reaction product simultaneously discharged from the reactor.

Surprisingly, when catalysts are produced in accordance with the process of the present invention, the productivity is increased and the production costs are reduced in comparison with those catalysts made from pre-alloys formed by rapid solidification on rollers using unstructured cooling rollers. The reasons for the resulting increase in productivity and reduction in the production costs for the catalysts of the present invention are an increase in the bulk density of the rapidly solidified pre-alloy, the improved transportability by means of conveyor belts, conveyor screws or in an air stream, the reduction in the necessary cargo space during transportation, and the reduction or elimination of the outlay involved in grinding such alloys.

DETAILED DESCRIPTION OF THE DRAWINGS

Figure 1A:
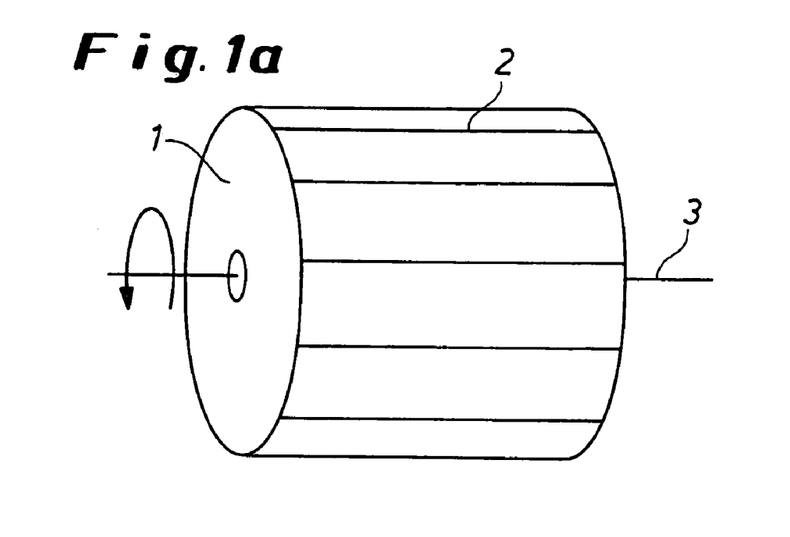
FIG. 1*a* illustrates a smooth cooling roller whose surface is structured with transverse grooves.

Reference will now be made to the Figures which illustrate different embodiments of the cooling rollers and the cooling plates of the present invention. Reference will now be made to FIG. 1a which is a side view of a rotating cooling roller 1. This cooling roller 1 has on its surface transverse grooves 2 which extend parallel to the axis of rotation 3 of the rotating cooling roller. Preferably, the transverse grooves 2 extend in the direction of the axis of rotation 3 of the cooling roller over the entire length or over a partial length of the cooling roller 1.

Figure 1B:
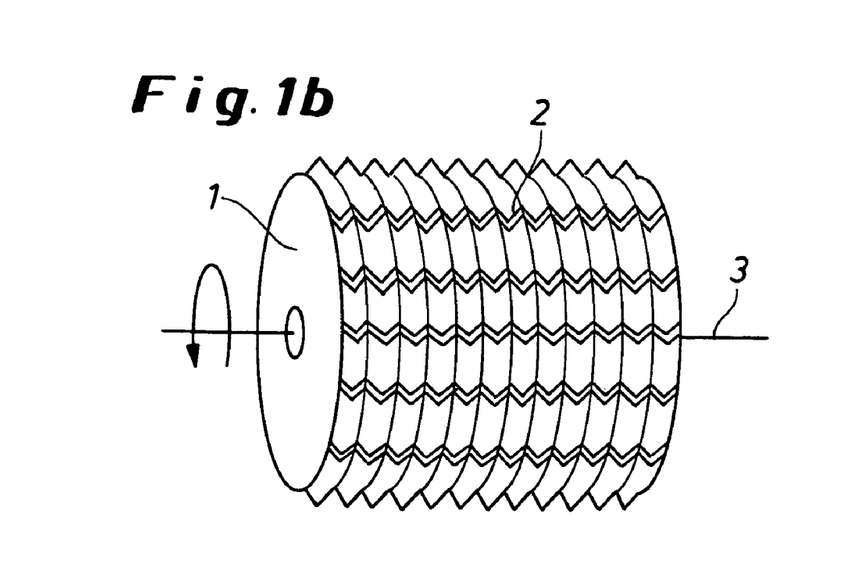
FIG. 1*b* illustrates a longitudinally structured cooling roller usually used for melt extraction/melt overflow processes, the surface of which cooling roller is structured with transverse grooves.

Reference will now be made to FIG. 1b which is a side view of a different embodiment of a rotating cooling roller 1. The rotating cooling roller 1 has on its surface transverse grooves 2 which extend parallel to the axis of rotation 3 of the rotating cooling roller. Preferably, the transverse grooves 2 extend in the direction of the axis of rotation 3 of the cooling roller over the entire length or over a partial length of the cooling roller 1.

Figure 2:
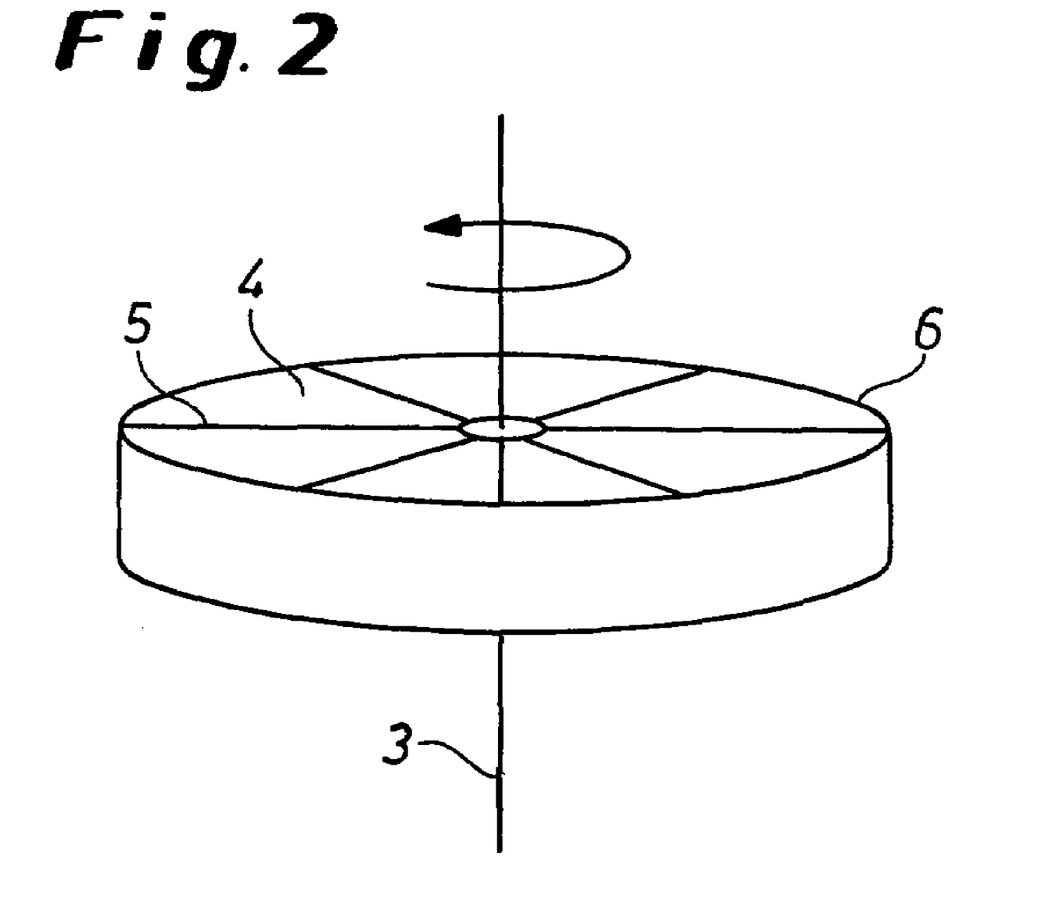
FIG. 2 illustrates a cooling plate having radially extending grooves

Reference will now be made to FIG. 2, a planar view of a rotating cooling plate. In this embodiment, a cooling plate 4 has radial grooves 5 which extend outwardly from the axis of rotation 3 to the edge 6 of the cooling plate.

Figure 3A:
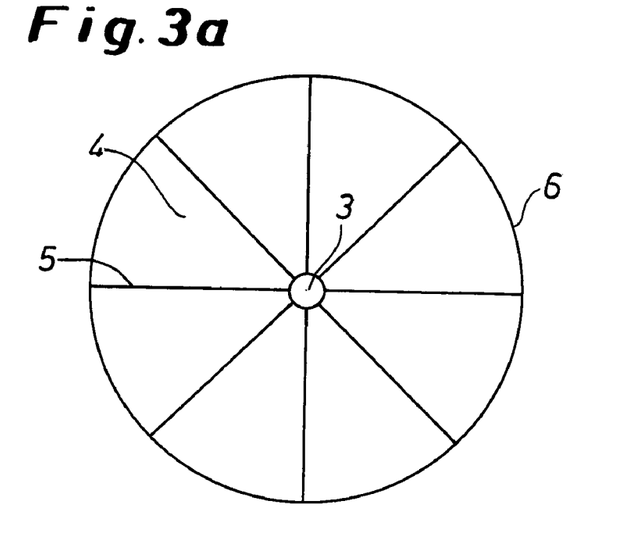
FIG. 3*a* illustrates a top view of a cooling plate having radially extending grooves.

Reference will now be made to FIG. 3a, a top view of a cooling plate. In this embodiment, the cooling plate 4 has grooves 5 which extend radially from the axis of rotation 3 to the edge 6 of the cooling plate 4.

Figure 3B:
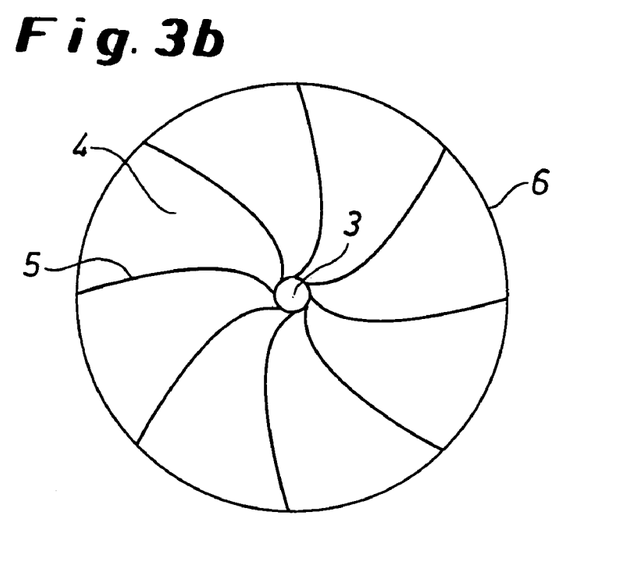
FIG. 3*b* illustrates a top view of a cooling plate having grooves extending in arc form.

Finally, reference will be made to FIG. 3b, a top view of another embodiment of a cooling plate of the invention. In this embodiment, the cooling plate 4 has grooves 5 extending in arc form from the axis of rotation 3 to the edge 6 of the cooling plate 4.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Production of Pre-Alloys

Example 1

According to the Invention

Production of the pre-alloy Al80Ni17Fe3 by rapid solidification in accordance with the melt overflow process with a cooling roller with surface structuring.

The amounts of aluminium, nickel and iron required to produce 20 kg of the pre-alloy (16 kg Al, 3.4 kg Ni, 0.6 kg Fe) were melted in an induction oven and then introduced into an inductively heated crucible. The melt was guided, in air, over a horizontal overflow edge onto an upwardly rotating structured cooling roller having transverse grooves, with the spacing of the transverse grooves being about 30 mm. The alloy particles which became detached from the cooling surface and flew off upwards were collected.

Example 1b

According to the Invention

Production of the pre-alloy Al71Ni26Fe3 by rapid solidification in accordance with the melt overflow process with a cooling roller with surface structuring.

The amounts of aluminium, nickel and iron required to produce 20 kg of the pre-alloy (14.2 kg Al, 5.2 kg Ni, 0.6 kg Fe) were melted in an induction oven and then introduced into an inductively heated crucible. The melt was guided, in air, over a horizontal overflow edge onto an upwardly rotating structured cooling roller having transverse grooves, with the spacing of the transverse grooves being about 30 mm. The alloy particles which became detached from the cooling surface and flew off upwards were collected.

These alloy particles have a length of about 30 mm and a thickness of about 0.1 mm.

Example 2

According to the Invention

Production of the pre-alloy Al80Ni17Fe3 by rapid solidification in accordance with the melt extraction process, using a cooling roller with surface structuring.

The amounts of aluminium, nickel and iron required to produce 10 kg of the pre-alloy (8 kg Al, 1.7 kg Ni, 0.3 kg Fe) were melted in an induction oven and then introduced into an inductively heated crucible. Fibers having a length of about 30 mm and a thickness of about 0.1 mm were removed from the melt, in air, by the immersion of a rotating structured cooling roller having transverse grooves wherein the spacing of the transverse grooves is about 30 mm. The alloy particles which became detached from the cooling surface and flew off in the direction of rotation were collected.

Example 3a

Not According to the Invention

Production of the pre-alloy Al80Ni17Fe3 by rapid solidification by pouring onto a cooling roller which was free of surface structuring.

The pre-alloy was melted in an induction oven in an aluminium oxide crucible, from 8000 g of aluminium, 1700 g of nickel and 300 g of iron, and poured into a copper mold. The total amount of the pre-alloy was about 10 kg. The ingots, pre-melted in bar form, were introduced into the crucible having a cast-on nozzle of a rapid solidification installation. The inductive melting of the pre-alloy was carried out in about 2 minutes with superheating of about 150° C. The melt was pressed by means of argon gas through 0.1 mm onto a rotating water-cooled copper roller which was free of surface structuring. The alloy strip which became detached from the roller surface once solidification had taken place was collected.

Example 3b

Not According to the Invention

Production of the pre-alloy Al80Ni17Fe3 by rapid solidification by pouring onto a cooling roller which was free of surface structuring.

The pre-alloy was melted from 800 g of aluminium, 170 g of nickel and 30 g of iron in an induction oven and placed in a rapid solidification installation. The inductive melting of the pre-alloy was carried out with superheating of about 100-150° C. The melt was pressed by means of argon gas through a broad nozzle onto a rotating water-cooled copper roller which was free of surface structuring. The alloy strip which became detached from the roller surface once solidification had taken place was collected.

Example 4

According to the Invention

Production of the pre-alloy Al80Ni17Fe3 by rapid solidification by pouring onto a cooling roller with surface structuring.

The amounts of aluminium, nickel and iron required to produce 60 kg of Al80Ni17Fe3 melt (48 kg Al, 10.2 kg Ni, 1.8 kg Fe) were melted in an induction oven and then introduced into a heatable crucible. The metal melt was poured through nozzles in the base of the crucible onto a rotating water-cooled cooling roller having transverse grooves, and which was located inside a vacuum chamber. The transverse grooves were spaced about 30 mm apart. Alloy particles having a length of about 30 mm and a thickness of about 0.1 mm were thereby formed by rapid solidification. The alloy particles which became detached from the cooling surface and flew off in the direction of rotation were collected.

Example 5

According to the Invention

Production of the pre-alloy Al71Ni26Fe3 by rapid solidification by pouring onto a cooling roller with surface structuring.

The amounts of aluminium, nickel and iron required to produce 60 kg of Al71Ni26Fe3 melt (42.6 kg Al, 15.6 kg Ni, 1.8 kg Fe) were melted in an induction oven, and then introduced into a heatable crucible. The metal melt was poured through nozzles in the base of the crucible onto a rotating water-cooled cooling roller having transverse grooves with the spacing of the transverse grooves being about 30 mm apart from each other, and which was located inside a vacuum chamber. Alloy particles having a length of about 30 mm and a thickness of about 0.1 mm were thereby formed by rapid solidification. The alloy particles which became detached from the cooling surface and flew off in the direction of rotation were collected.

Testing of the Pre-Alloys in Respect of Their Mechanical Properties

The pre-alloys produced in Examples 1 to 5 were tested for bulk density, mean particle size and transport properties. The bulk density was determined by weighing a defined volume (i.e. 2 liters) of pre-alloy. In order to assess the pourability, the pre-alloy was shaken out of the measuring vessel with gentle shaking. In the case of pronounced matting, the contents of the vessel could only be shaken out as a whole. In the case of either limited pourability or in the case of pourability, individual particle agglomerates or free-flowing individual particles could be shaken out, respectively. The mean particle size was determined by repeated measurement of the particles using a caliber gauge (to assess width, length) or by electron microscopic sectional images (to assess thickness).

The results of the tests are summarised in Table 1:

TABLE 1

| Example | Alloy | Bulk density | Mean particle size | Transport properties |
|---|---|---|---|---|
| 1 | Al80Ni17Fe3 rapidly solidified by the melt overflow process (with transverse grooves, according to the invention) | 0.32 kg/l | 0.1 × 0.2 × 28 mm | pourable no matting |
| 1b | Al71Ni26Fe3 rapidly solidified by the melt overflow process (with transverse grooves, according to the invention) | 0.38 kg/l | 0.1 × 0.2 × 26 mm | pourability no matting |
| 2 | Al80Ni17Fe3 rapidly solidified by melt extraction (with transverse grooves, according to the invention) | 0.30 kg/l | 0.1 × 0.1 × 24 mm | pourable no matting |
| 3a | Al80Ni17Fe3 rapidly solidified by pouring onto a roller (without transverse grooves, not according to the invention) | 0.06 kg/l | 0.1 × 25 × 112 mm | not pourable pronounced matting |
| 3b | Al80Ni17Fe3 rapidly solidified by pouring onto a roller (without transverse grooves, not according to the invention) | 0.08 kg/l | 0.1 × 3 × 84 mm | not pourable pronounced matting |
| 4 | Al80Ni17Fe3 rapidly solidified by pouring onto a roller (with transverse grooves, according to the invention) | 0.26 kg/l | 0.1 × 3 × 27 mm | limited pourability no matting |
| 5 | Al71Ni26Fe3 rapidly solidified by pouring onto a roller (with transverse grooves, according to the invention) | 0.35 kg/l | 0.1 × 3 × 22 mm | limited pourability no matting |

Production of a Catalyst from the Pre-Alloys

Example 6

782 g of sodium hydroxide were dissolved in 3129 g of water, and the temperature of the resulting sodium hydroxide solution was adjusted to 80° C. Under a layer of nitrogen, 200 g of the comminuted pulverulent starting alloy were added to the sodium hydroxide solution in such a manner that the temperature was maintained at 80±2° C. and the formation of foam was not too pronounced. The reaction mixture was then stirred for 30 minutes at about 80° C. Thereafter, the supernatant lye was decanted off and the residue was then treated for 5 minutes, with stirring, with a solution of 78 g of sodium hydroxide in 313 g of water. This lye was also decanted off and the catalyst was washed with water to a pH value of 8 to 9. The catalyst was obtained quantitatively in the form of an aqueous slurry.

Hydrogenation of Dinitrotoluene (DNT)

An autoclave having a volume of 1000 ml and equipped with a gassing stirrer, a hydrogen supply pipe, an inlet pipe for the nitro compound and an outlet valve for excess hydrogen was used. The reaction mixture left the reactor through a frit, which retained the catalyst. The temperature in the reactor was regulated by means of an external heating or cooling circuit. A coiled cooling pipe inside the reactor provided additional cooling of the reaction mixture. 480 g of a commercial mixture comprising a mixture of 80% 2,4-diaminotoluene and 20% 2,6-diaminotoluene (TDA) with water in a weight ratio of TDA to water of 63:37 as well as 5.0 g-6.5 g of catalyst were placed in the reactor. The contents of the reactor were then placed under pressure by means of hydrogen and heated. At a temperature of 180° C. and a pressure of 26 bar, 125 g/h of a commercial mixture of 80% 2,4-dinitrotoluene and 20% 2,6-dinitrotoluene were passed into the reactor hourly and hydrogenation was carried out until the catalyst was exhausted. The resulting hydrogenation product was removed from the reactor continuously and worked up to form the pure diaminotoluene isomeric mixture.

Different Raney nickel catalysts were tested in a series of hydrogenation tests. The results are shown in Table 2. The catalysts tested are characterised in Table 2 by the composition of their pre-alloy and the nature of their rapid solidification. Raney nickel catalysts were then produced analogously to Example 6 from the pre-alloys so produced. Examples 7 and 8 were carried out using catalysts which were not produced according to the invention, and Examples 9 to 12 were carried out using catalysts produced according to the invention.

A comparison of Examples 7, 8, 9 and 10 shows that the catalysts produced according to the invention having the same composition achieve higher yields of toluene diamine (TDA) in the hydrogenation of DNT (dinitrotoluene) and have longer catalyst lifetimes.

TABLE 2

| Example | Alloy | Structure/ Production of the catalyst | TDA yield % of theory | Useful life h |
|---|---|---|---|---|
| 7 | Al80Ni17Fe3 (corresponds to Example 3a) | microcrystalline/ rapid solidification on an unstructured cooling roller | 97.6 | 128 |
| 8 | Al80Ni17Fe3 (corresponds to Example 3b) | microcrystalline/ rapid solidification on an unstructured cooling roller | 98.0 | 78 |
| 9 | Al80Ni17Fe3 (corresponds to Example 4) | microcrystalline/ rapid solidification on a structured cooling roller | 98.4 | 153 |
| 10 | Al80Ni17Fe3 (corresponds to Example 2) | microcrystalline/ rapid solidification by melt extraction (by means of a cooling roller structured with transverse grooves) | 98.2 | 240 |
| 11 | Al71Ni26Fe3 (corresponds to Example 5) | microcrystalline/ rapid solidification on a structured cooling roller | 98.4 | 248 |
| 12 | Al71Ni26Fe3 (corresponds to Example 1b) | microcrystalline/rapid solidification by the melt overflow process (by means of a cooling roller structured with transverse grooves) | 98.1 | 210 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of Raney nickel catalysts, comprising
    (1) contacting (a) the melt of an alloy which comprises (i) from 40 to 95 wt. % aluminum, (ii) from 5 to 50 wt. % nickel, (iii) from 0 to 20 wt. % iron, (iv) from 0 to 15 wt. % of one or more transition metals selected from the group consisting of cerium, cerium mixed metal, vanadium, niobium, tantalum, chromium, molybdenum and manganese, and, (v) optionally, additional glass-forming elements; with (b) one or more rotating cooling rollers or cooling plates, wherein the surface of said cooling rollers is structured by means of transverse grooves and the surface of said cooling plates is structured by means of grooves which extend outwardly from the axis of rotation,
    (2) allowing the melt to cool and solidify on said rotating cooling rollers or cooling plates; and
    (3) treating the rapidly solidified alloy with one or more organic bases and/or inorganic bases.

2. The process of claim 1, wherein said contacting comprises overflowing of the melt formed in the melt overflow process from a melting crucible onto a rotating cooling roller.

3. The process of claim 1, wherein said contacting comprises dipping a rotating cooling roller which is positioned above the alloy into the melt formed, thereby removing a portion of the alloy melt formed, and allowing the to cool and solidify on the cooling roller, in which the surface of the rotating cooling roller has transverse grooves.

4. The process of claim 1, wherein said contacting comprises pouring the melt onto a rotating cooling roller or into the gap between two cooling rollers which are rotating in opposite directions.

5. The process of claim 1, wherein said contacting comprises pouring of the melt onto a rotating cooling plate.

* * * * *